US007931020B2

(12) United States Patent
Trees et al.

(10) Patent No.: US 7,931,020 B2
(45) Date of Patent: Apr. 26, 2011

(54) DISSOCIATED DISCHARGE EHD SPRAYER WITH ELECTRIC FIELD SHIELD

(75) Inventors: Gregory A. Trees, Columbus, OH (US); Jason Chungyin Fong, Hong Kong (HK)

(73) Assignee: Battelle Memorial Institute, Columbus, OH (US)

(*) Notice: Subject to any disclaimer, the term of this patent is extended or adjusted under 35 U.S.C. 154(b) by 1196 days.

(21) Appl. No.: 11/560,542

(22) Filed: Nov. 16, 2006

(65) Prior Publication Data

US 2008/0308095 A1 Dec. 18, 2008

Related U.S. Application Data

(60) Provisional application No. 60/773,239, filed on Feb. 14, 2006.

(51) Int. Cl.
*A61M 11/00* (2006.01)
(52) U.S. Cl. .................................................. 128/200.14
(58) Field of Classification Search ............. 128/200.16, 128/200.23, 203.12, 203.24, 204.25, 200.14; 239/692; 427/483
See application file for complete search history.

(56) References Cited

U.S. PATENT DOCUMENTS 4,004,733 A 1/1977 Law
4,356,528 A 10/1982 Coffee
4,358,059 A 11/1982 Coffee .......................... 239/691
4,362,775 A 12/1982 Yabe et al.
4,470,550 A 9/1984 Coffee .......................... 239/697
4,549,243 A 10/1985 Owen et al. ................... 361/228
4,561,037 A 12/1985 MacLaine et al. ............ 361/228
4,634,057 A 1/1987 Coffee et al. ................. 239/690
4,659,012 A 4/1987 Coffee
4,663,639 A 5/1987 Owen et al. ..................... 347/55
4,703,891 A 11/1987 Jackson et al. ................ 239/171
4,801,086 A 1/1989 Noakes ............................. 239/3
4,829,996 A 5/1989 Noakes et al. ........... 128/200.14
4,962,885 A 10/1990 Coffee ............................. 239/3
5,044,564 A 9/1991 Sickles
5,121,884 A 6/1992 Noakes ......................... 239/691
5,184,778 A 2/1993 Noakes ......................... 239/691
5,222,663 A 6/1993 Noakes et al. .................... 239/3
5,222,664 A 6/1993 Noakes et al. .................... 239/3
5,704,554 A 1/1998 Cooper et al.
5,788,166 A 8/1998 Valaskovic et al. ........... 239/708
5,810,265 A 9/1998 Cornelius et al. ............. 239/690
5,927,618 A 7/1999 Jefferies et al. ............ 239/690.1
5,932,011 A 8/1999 Noakes et al. ................ 118/629
6,068,199 A 5/2000 Coffee ............................. 239/3

(Continued)

FOREIGN PATENT DOCUMENTS

EP 0054730 6/1982

(Continued)

OTHER PUBLICATIONS

U.S. Appl. No. 60/773,272, filed Feb. 14, 2006, Gaydos et al.

(Continued)

*Primary Examiner* — Tatyana Zalukaeva
*Assistant Examiner* — Kristen C Matter
(74) *Attorney, Agent, or Firm* — Stevens & Showalter LLP (57) ABSTRACT

The invention is directed to devices and methods for electrohydrodynamic (EHD) aerosolization of liquids utilizing a dissociated discharge electrode and an electric field shield disposed between the nozzle and the discharge electrode. Preferred embodiments are designed as inhalers suitable for administration of therapeutic compounds to the respiratory tract of a patient, preferably the lungs.

43 Claims, 6 Drawing Sheets

U.S. PATENT DOCUMENTS

| | | |
|---|---|---|
| 6,079,634 A | 6/2000 | Noakes et al. .................... 239/3 |
| 6,105,571 A | 8/2000 | Coffee .................... 128/200.14 |
| 6,138,671 A | 10/2000 | Noakes et al. ........... 128/202.25 |
| 6,145,391 A | 11/2000 | Pui et al. ....................... 73/865.5 |
| 6,286,725 B1 | 9/2001 | Gerber ......................... 222/207 |
| 6,302,331 B1 | 10/2001 | Dvorsky et al. ................... 239/3 |
| 6,311,903 B1 | 11/2001 | Gaw et al. .................... 239/690 |
| 6,318,640 B1 | 11/2001 | Coffee ............................ 239/3 |
| 6,318,647 B1 | 11/2001 | Gaw et al. .................... 239/690 |
| 6,368,079 B2 | 4/2002 | Peters et al. ............... 417/413.2 |
| 6,386,195 B1 | 5/2002 | Coffee |
| 6,397,838 B1 | 6/2002 | Zimlich, Jr. et al. ..... 128/200.14 |
| 6,454,193 B1 | 9/2002 | Busick et al. ................. 239/690 |
| 6,457,470 B1 | 10/2002 | Coffee |
| 6,491,897 B1 | 12/2002 | Freund et al. .................... 424/45 |
| 6,503,481 B1 | 1/2003 | Thurston et al. ................ 424/45 |
| 6,595,208 B1 | 7/2003 | Coffee et al. ............ 128/203.12 |
| 6,660,715 B2 | 12/2003 | Klibanov ........................... 514/2 |
| 6,684,879 B1 | 2/2004 | Coffee et al. |
| 6,796,303 B2 | 9/2004 | Zimlich et al. ........... 128/200.14 |
| 6,827,559 B2 | 12/2004 | Peters et al. ............... 417/413.2 |
| 6,880,554 B1 | 4/2005 | Coffee |
| 2003/0216471 A1 | 11/2003 | Dahl et al. |
| 2004/0001655 A1 | 1/2004 | Proicou et al. ................ 383/202 |
| 2004/0195403 A1 | 10/2004 | Atterbury et al. ............. 239/690 |
| 2008/0308580 A1 | 12/2008 | Gaydos et al. |

FOREIGN PATENT DOCUMENTS

| | | |
|---|---|---|
| GB | 261 827 A | 11/1926 |
| GB | 2018627 | 10/1979 |
| WO | 99/07478 A1 | 2/1999 |
| WO | WO 03/072263 A1 | 9/2003 |
| WO | 2004/078244 A1 | 9/2004 |
| WO | 2007094833 | 8/2007 |
| WO | 2007094835 | 8/2007 |

OTHER PUBLICATIONS

U.S. Appl. No. 60/699,932, filed Jul. 15, 2005, Lipp et al.
U.S. Appl. No. 11/560,540, filed Nov. 16, 2006, Gaydos et al.
Cloupeau, M. et al., "Electrohydrodynamic Spraying Functioning Modes: A Critical Review," *J Aerosol Sci.*, 1994, 25(6), pp. 1021, 1025-1026.
International Search Report No. PCT/US2006/044626 date of mailing Mar. 26, 2007.

DISSOCIATED DISCHARGE EHD SPRAYER WITH ELECTRIC FIELD SHIELD

CROSS REFERENCE TO RELATED APPLICATIONS

This application claims priority of U.S. Provisional Patent Application No. 60/773,239, filed Feb. 14, 2006, the entirety of which is hereby incorporated herein by reference for all purposes.

The subject matter disclosed herein is related to the subject matter disclosed in commonly assigned U.S. Provisional Patent Application No. 60/773,272, filed Feb. 14, 2006, entitled "ACCURATE METERING SYSTEM," the contents of which are also incorporated herein by reference for all purposes.

FIELD OF THE INVENTION

This invention relates to devices and methods for spraying a liquid and specifically to devices and methods for aerosolization of liquids using an electric field, often referred to as electrohydrodynamic (EHD) aerosolization.

BACKGROUND OF THE INVENTION

Electrostatic spraying devices, in which an electric charge is imparted to a liquid before or after it is forced through a nozzle, to provide small, electrostatically charged droplets, are widely known and used for a variety of purposes, including spraying of paint and chemicals. These may be distinguished from electrohydrodynamic (EHD) devices, in which an electric charge of sufficient intensity is applied to the fluid to induce aerosolization.

Coffee, U.S. Pat. No. 4,962,885, for example, describes an apparatus that comprises a conductive nozzle charged to a potential of up to 20,000 volts closely adjacent a grounded electrode. The electric field generated between the nozzle and the grounded electrode is sufficiently intense to atomize liquid delivered to the nozzle into finely charged particles. Dvorsky et al., U.S. Pat. No. 6,302,331 describes a system in which fluid is delivered to a nozzle that is maintained at high electric potential relative to a proximate electrode to cause aerosolization of the fluid, with the fluid emerging from the nozzle in the form of a so-called Taylor cone (as described, for example, in M. Cloupeau and B. Prunet-Foch, "Electrohydrodynamic Spraying Functioning Modes: A Critical Review," J Aerosol Sci., Vol. 25, No. 6, pp. 1021, 1025-1026 (1994)). The Taylor cone shape of the dispensed aerosolized fluid results from a balance of the forces of electric charge on the fluid and the fluids own surface tension. Desirably, the charge on the fluid overcomes the surface tension at the tip of the Taylor cone, so that a thin jet of fluid forms, which separates a short distance from tip into a fine aerosol having uniform droplet size.

More recently, there has been a recognition that EHD devices are useful for producing and delivering aerosols of therapeutic products for inhalation by patients. Inhalation therapy for delivering both locally and systemically active drug compounds is increasing as the health-care community recognizes the benefits this route offers to patients. EHD aerosol delivery systems are expected to revolutionize inhalation therapy. These systems are more efficient and reproducible than existing inhalation devices. EHD devices can deliver a soft (isokinetic) cloud of uniformly sized particles directly to the lungs with better than 90 percent efficiency, and without the need for liquid propellants or other pressurized systems. The aerosol is delivered using the patient's own breath (inspiration), whereby the patient can easily achieve the drug delivery at normal inhalation rates. The delivery mechanism is especially suited to use with infants, young children, seniors, and patients with an impaired respiratory function.

Zimlich, Jr., et al., U.S. Pat. No. 6,397,838 discloses a pulmonary aerosol delivery device that delivers an aerosolized liquid cloud having therapeutic properties to a user's lungs. The compact and convenient device includes a housing of such size that it can be held in a user's one hand with an exit opening in the housing for directing the aerosol to the user's mouth. The aerosolizing apparatus (i.e., EHD nozzle) includes a plurality of spray sites (i.e., tip ends) that cooperate with discharge electrodes and reference electrodes downstream respectively of the tip ends to result in an aerosolized spray from at least one tip end. The multiple spray site nozzle can achieve larger dosages.

While U.S. Pat. No. 6,397,838 presents a significant advance over previously known aerosol delivery devices, opportunities exist for improvement. For instance, in the device described in the '838 patent, the EHD nozzle is to be pointed downwardly in order for each nozzle tip to dispense consistently. However, most users prefer to be upright when using the dispenser. Consequently, the dispensed aerosolized liquid had to be directed through a bend to the exit opening. Momentum of the aerosolized droplets tends to deposit some of liquid onto the exit opening, reducing the effective dose delivered to the user. In addition, wetting of the interior of the EHD nozzle itself may degrade performance. Since most, if not all, liquids dispensed by pulmonary delivery devices to some extent are conductive, wetting tends to dissipate the desired electric fields within the EHD nozzle, especially if a conduction path should form between the discharge and reference electrodes.

Atterbury et al., published U.S. application no. US 2004/0195403 A1 provides some solutions to the wetting of the interior of the nozzle through shielding of discharge electrodes. Branching channels formed in the spray nozzle provide a controlled pressure drop to a plurality of circumferentially arranged nozzle tips. The controlled pressure drop to each nozzle tip advantageously allows increased dosage production with multiple tips while avoiding undesired variations in the flow rate seen at each nozzle tip, which would affect the achieved particle size. One or more dissociated discharge electrodes, shielded from the spray nozzle, may be positioned upstream or downstream of the plane of the nozzle tip of the spray nozzle, which preferably neutralizes the charge applied to the atomized droplets. It is desirable to have an EHD nozzle that produces a completely electrically neutralized aerosolized liquid, since droplets that retain a charge tend to compound wetting problems and may also limit the therapeutic effect of the inhaler.

We have discovered, however, that the system described by Atterbury et al. can be improved upon. In particular, in embodiments where the discharge electrode is upstream of the nozzle, there is a tendency for the insulating shield located between the nozzle and the discharge electrode to be wetted, as droplets of atomized liquid are "pulled" by the nature of the electric field back towards the discharge electrode. Consequently, a need exists for an improved EHD nozzle that provides more efficient delivery of a consistent dose of aerosolized particles, particularly one that is suitable for use in a portable pulmonary aerosol delivery device.

SUMMARY OF THE INVENTION

In one aspect, the invention is directed to a device for dispensing an aerosolized liquid. The device comprises a voltage power source having a first pole and a second pole, and a flow pathway extending between an upstream gas intake and a downstream aerosol egress, with at least one nozzle disposed therein. The nozzle has a supply end for receiving fluid to be sprayed, and a forward spray end. One or more discharge electrodes operatively connected to the first pole of the voltage power source capable of providing high voltage is also disposed within the air flow pathway. A conductive electric field shield that is operatively connected to ground or to the second pole of the voltage power source is disposed between the nozzle and the discharge electrode, and an insulator is disposed between the discharge electrode and the conductive electric field shield.

Another aspect of the invention is directed to a method of providing an aerosol, said method comprising the steps of (a) providing a device as set forth above, (b) initiating flow of a gas through the flow pathway and supplying liquid to the nozzle, and (c) applying voltage to the discharge electrode in an amount sufficient to ionize at least a portion of the gas, wherein the electric field created by the difference in electric potential between the discharge electrode and the liquid is of sufficient intensity to aerosolize the liquid.

A further aspect of the invention is directed to a electrohydrodynamic spraying method comprising the steps of (a) supplying a liquid to be sprayed as an aerosol to a nozzle having a supply end and a plurality of spray ends, (b) supplying a voltage power source having a first pole and a second pole, (c) applying a voltage from the first pole of the voltage power source to a discharge electrode positioned upstream of the nozzle, (d) transporting a gas across the discharge electrode to create a cloud of positively charged ions in the vicinity of said nozzle, and (e) positioning a conductive electric field shield in electric communication with the liquid between the nozzle and the discharge electrode, wherein the electric field shield is at ground potential or supplied with a voltage from the second pole of the voltage power source.

BRIEF DESCRIPTION OF THE FIGURES

The accompanying drawings, which are incorporated in and constitute a part of this specification, illustrate embodiments of the invention, and, together with the general description of the invention given above, and the detailed description of the illustrative embodiments that follows, serve to explain the principles of the present invention.

DETAILED DESCRIPTION OF ILLUSTRATIVE EMBODIMENTS

The instant invention is directed, in particular, to devices and methods for generating an aerosol utilizing a dissociated discharge electrode to provide EHD aerosolization. As described above, an EHD apparatus aerosolizes liquid by exposing the liquid to a region of high electric field strength, which imparts a net electric charge to the liquid. In the present invention, the region of high electric field strength typically is provided by a voltage potential difference between the discharge electrode and the liquid in the nozzle. In response to this field, charges are imposed on the surface of the liquid, which causes molecules of the liquid to repel each other. This force works against the surface tension of the liquid. If the surface charge is high enough, the fluid will be formed into a cone. If the electrical force exerted on the liquid surface is sufficient to overcome the surface tension, a jet is formed at the apex of the cone which ultimately breaks into droplets of more or less uniform size. These droplets collectively form a cloud.

As used herein, the term "discharge electrode" means a conductive element that, when highly charged, is capable of ionizing at least a portion of the gas that passes over it. Multiple discharge electrodes may be utilized, so that there are a plurality of separate interconnected elements disposed within the gas flow pathway, or the discharge electrode may alternatively comprise a conductive band or annulus that has a plurality of sharply pointed projections to more efficiently concentrate the static charge at numerous points around the band. The band may be made of a metal, such as copper or stainless steel, highly conductive plastic, or other highly conductive materials may be utilized. Other suitable mechanisms for creating a cloud of ionized gas as described above, besides those mentioned herein, may also be used, as would be known to those of ordinary skill in the art.

The devices of the present invention further comprise at least one nozzle, having a supply end and a forward spray end. Multiple nozzles may be used, or the device may comprise a single nozzle having one or more spray sites, with a forward spray end at the end of each spray site. A preferred nozzle is one having a plurality of spray sites, such as from 12 to 40, preferably 16 or 24, in an annular ring configuration. The nozzle may be conductive or non conductive. Conductive nozzles may be prepared from metal, or from a conductive polymer, such as, for example, acrylonitrile butadiene styrene (ABS) filled with 10% carbon fibers. Non-conductive nozzles may be prepared from a wide variety of synthetic polymers, well known to those of ordinary skill in the art.

The devices of the present invention further comprise a voltage power source having a first pole and a second pole. The discharge electrode is operatively connected to either the first pole or the second pole of the power source, which acts to provide a positive or negative charge to the electrode, or maintain the electrode at ground potential. In preferred embodiments, the discharge electrode is positively charged, and the nozzle, or the liquid contained therein is maintained at ground potential. Thus, in this embodiment, gas is drawn over the discharge electrode, producing a cloud of positively charged ions forward of the nozzle. As used herein, "forward" or "in front of" means in the downstream direction, towards the egress from which the aerosol exits the device. The potential difference between the cloud of ions and the liquid in the nozzle induces a charge in the liquid at the nozzle of sufficient magnitude to produce EHD aerosolization Alternatively, a voltage charge from the power source may be applied both to the discharge electrode and to the nozzle (if the nozzle is prepared from a conductive material), or to the liquid being supplied to the nozzle. In these configurations, the polarity applied to the nozzle (or the liquid supplied thereto) is opposite to that of the charge applied to the discharge electrode and is provided by the first and second poles of the power source. Because the first and second poles are capable of providing opposite charges, only one power source may be required. Whichever embodiment, sufficient voltage must be applied to create a potential between the discharge electrode and the liquid at the spray end of the nozzle adequate to produce a jet at the apex of the cone which breaks into droplets of more or less uniform size. Preferably, the potential difference is on the order of from about 5 to about 15 kV, more preferably from about 7 to about 12 kV.

Figure 1A:
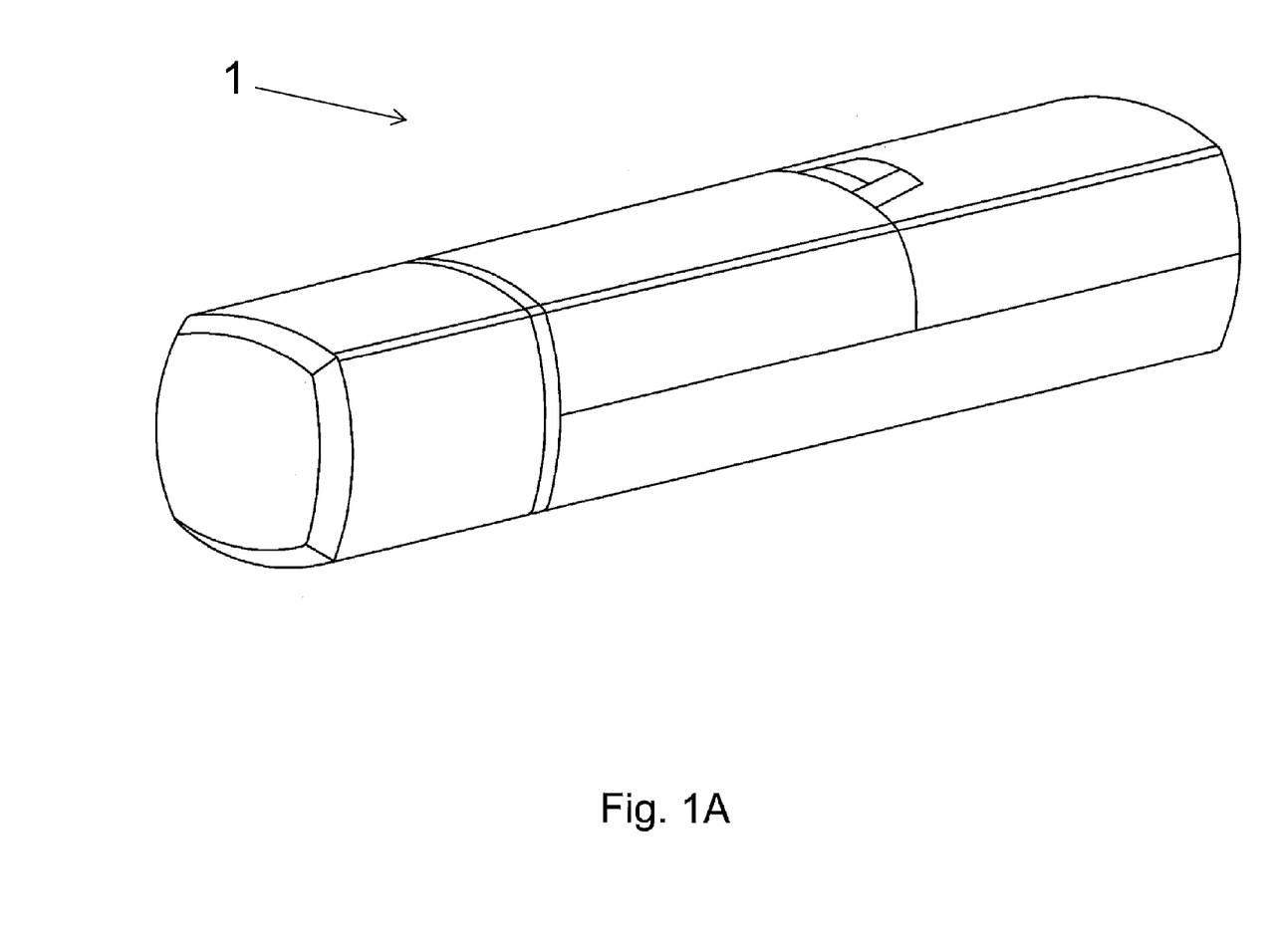
FIGS. 1a-c depict exemplary dispensing devices in the form of hand held inhalers.
Figure 1B:
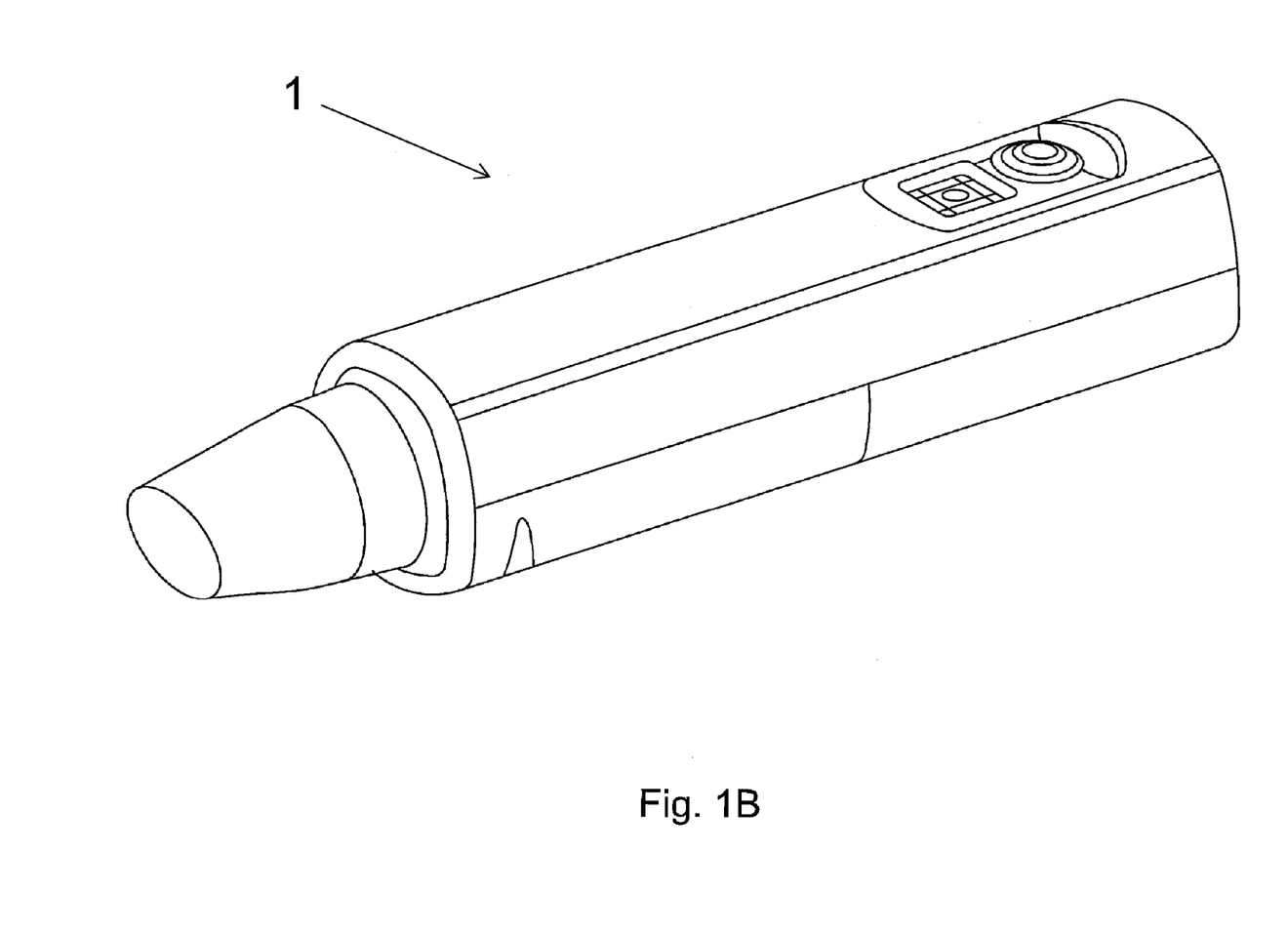
Figure 1C:
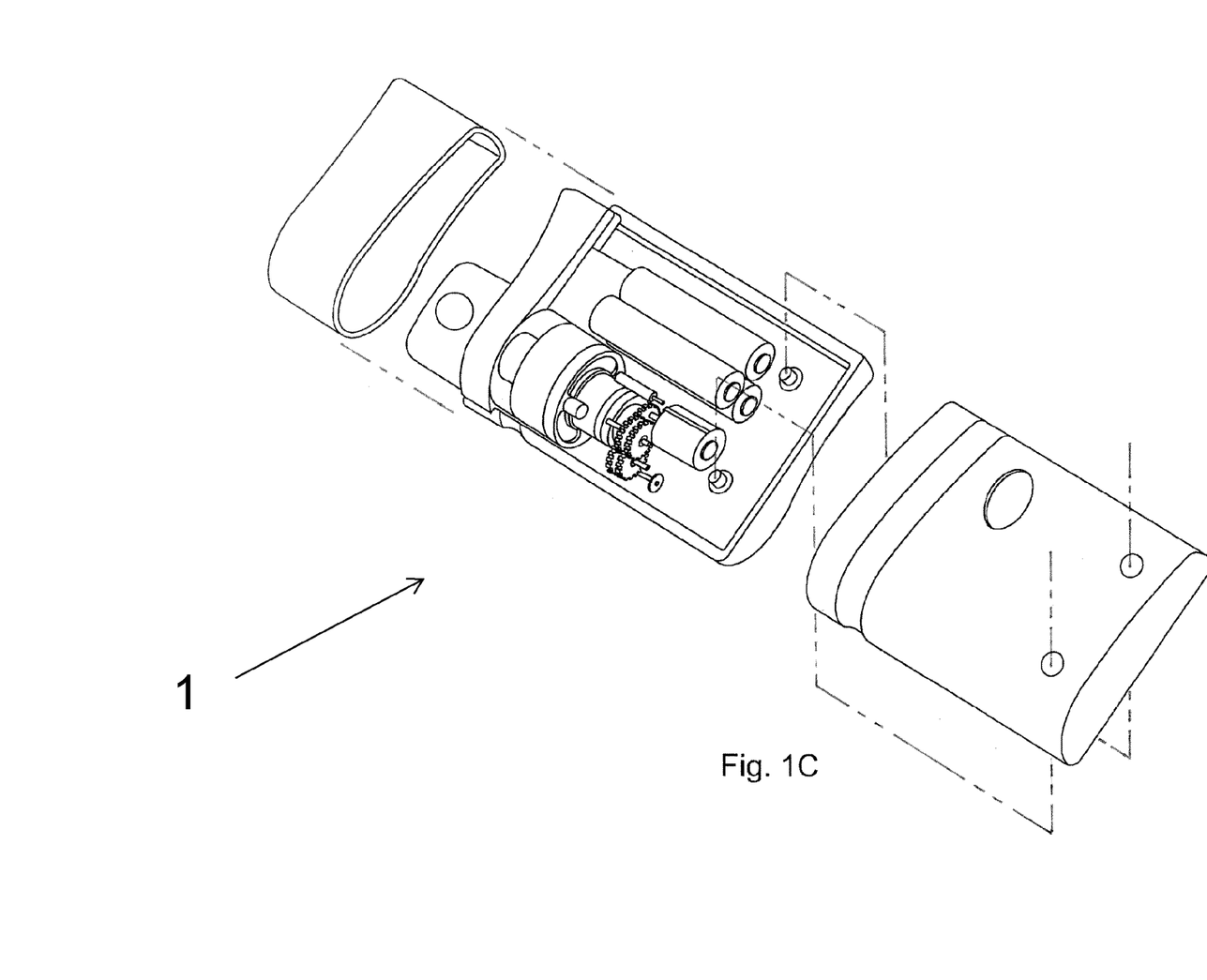

The discharge electrode is disposed within a flow pathway that extends between an upstream gas intake and a downstream aerosol egress. The flow pathway may be formed as a distinct channel within the device, through which gas can flow, or may simply be delimited by the outer housing of the device. The term "gas intake," as used herein, refers to the site at which gas enters the flow path, while the term "aerosol egress" refers to the site at which aerosolized liquid exits the flow path. Thus, the flow pathway may also include a mixing zone, located forward of the nozzle. When a voltage is applied to the discharge electrode, a cloud of ions is created in the gas passing over the discharge electrode. This cloud of charged ions may then intermix with droplets of aerosolized liquid bearing the opposite charge in the mixing zone, thereby reducing, or effectively eliminating the net charge on droplets in the aerosol cloud. In devices designed as inhalers, the aerosol egress may be located in a mouthpiece. Alternatively, the inhaler may be designed for nasal inhalation, and the aerosol egress may be an opening small enough to fit into the nares of a patient. FIGS. 1a to 1c depict examples of portable, hand held inhalers of the present invention.

Liquid is provided to the nozzle concurrently with the creation of the electric field. As used herein the term "liquid" is intended to encompass all types of liquid solutions, suspensions, dispersions and emulsions. A wide variety of liquid supply means suitable for use in the present invention are known to those of ordinary skill in the art. Preferably, the liquid to be aerosolized is held in a containment vessel or reservoir that stores and maintains the integrity of any ingredients dissolved or suspended in the liquid. The containment vessel may take the form of a holder for a liquid enclosed in single dose units, a plurality of sealed chambers each holding a single dose of the liquid, or a vial for enclosing a bulk supply of the liquid. The containment vessel preferably is physically and chemically compatible with any therapeutic or active agent in the liquid, and is preferably airtight. Suitable containment vessels are further described, for example, in Proicou et al, U.S. published application no. US 2004/0001655 A1.

The devices of the present invention also preferably contain means for supplying liquid to the nozzle. The liquid supplier preferably includes means for providing consistent delivery of the desired amount of liquid to the nozzle, at a desired pressure and flow rate. A wide variety of mechanisms for providing controlled delivery of fluid are known to those of skill in the art. For example, the liquid supplier may include a pump and valve mechanism as described, for example, in U.S. Pat. Nos. 4,634,057, 6,368,079, 6,827,559. A preferred valve mechanism is described, for example, in U.S. Pat. No. 6,286,725. Another preferred liquid supply mechanism is described in U.S. Patent Application No. 60/773272, filed on the same date as the instant application and entitled "ACCURATE METERING SYSTEM."

Figure 2:
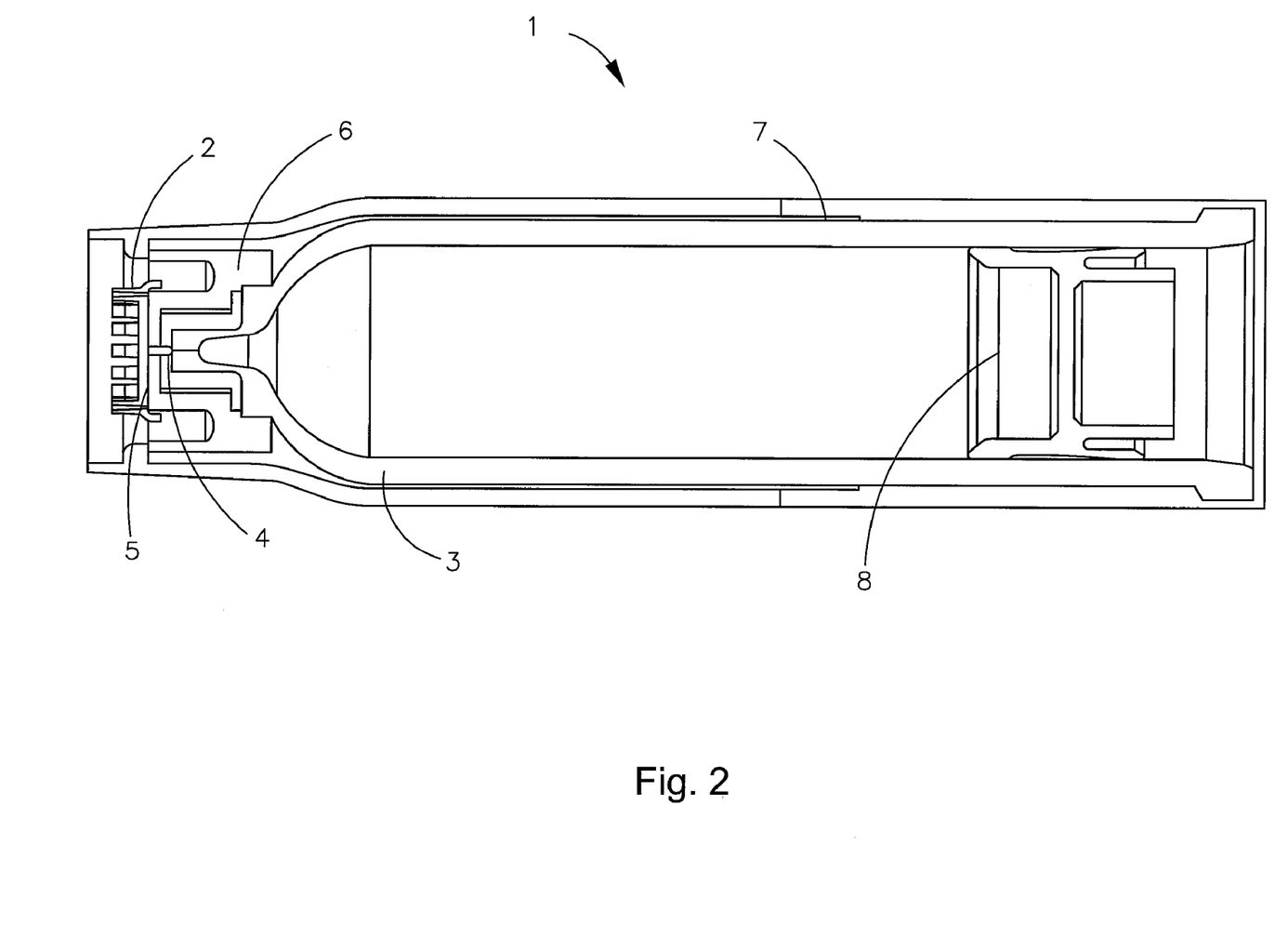
FIG. 2 depicts certain components of another exemplary dispensing device.

FIG. 2 shows a cross section of an exemplary liquid supplier and nozzle suitable for use in the present invention. This figure depicts a cartridge (1) comprising an insulator (2) which houses a reservoir (3). Liquid passes from the reservoir through supply tube (4) into nozzle (5), which is mounted on conductive back (6). Disposed between insulator (2) and reservoir (3) is a cylindrical electric field shield (7). In this example, plunger (8) is driven by a leadscrew (not shown), to supply liquid to the nozzle at a desired volume and rate.

In the devices and methods of the present invention, liquid is preferably supplied to the nozzle at a rate that allows complete aerosolization of any liquid discharged from the nozzle. This rate will depend on the particular liquid selected, as particular characteristics of the fluid, such as surface tension, viscosity, electrical permittivity and resistivity will all play a part in determining the rate and efficiency of EHD aerosolization. Liquids amenable to aerosolization by electrohydrodynamic spraying generally are characterized by particular electrical and physical properties.

As would be apparent to those skilled in the art, the voltage and current applied to the discharge electrode may be modified, depending on the liquid being delivered, to achieve optimal aerosolization. The device may utilize a power supply having a variable or fixed output. For example, a power supply adapted to regulate an electrical characteristic of its output, depending on various operating conditions, may be employed, as described, for example, in co-owned U.S. Provisional Application No. 60/699,932, entitled Improved Dispensing Device and Method, filed Jul. 15, 2005.

The physical properties of the liquid composition typically comprise: (i) a surface tension of about 10 to 72 milliNewtons/meter; (ii) an electrical resistivity of about 5 to 100,000 ohm-meters; and (iii) and an electrical permittivity of about 5 to 500. It may be possible to achieve a liquid composition with physical properties falling within these parameters by simply combining an active ingredient with a carrier material. However, if the combination of active ingredient and carrier material does not produce a liquid composition having physical properties falling within these parameters, an aerosol properties adjusting material may be included to bring the composition within the desired parameters. Suitable aerosol properties adjusting materials include the following materials or their derivatives; ethanol or other alcohols; propylene glycol; polyethylene glycol; glycerol; oleic acid; medium chain triglycerides; fatty acids; soybean oil; olive oil; phospholipids, and perfluorocarbons.

The liquid compositions to be sprayed may also include one or more optional excipients. The excipient may be included for a variety of purposes including: stabilization of the liquid composition or the therapeutic agent; facilitating control of aerosol particle size; increasing the solubility of the active ingredient in the composition; lowering the surface tension of the liquid; controlling osmolality; and sweeting or flavoring the composition. Suitable excipients include, inter alia: celluloses; polyvinyl pyrrolidone (povidone or PVP); polyvinyl alcohol (PVA); triglycerides; ethoxylated oils; polyethylene glycol; saccharide gums; alginates; oils; glycerides; polysorbates; lecithins; antioxidants, such as ascorbic acid, ascorbic acid esters, Vitamin E and other tocopherols, butylated hydroxyanisole, and butylated hydroxytoluene; chelating or complexing agents such as EDTA; preservatives such as benzalkonium chlorides, phenol, parabens, or any other acceptable antimicrobial or antifungal agent; sodium chloride, sodium acetate; poloaxamers; sorbitan esters; glycerides; ethoxylated alcohols; ethoxylated phenols; ethylene oxide-propylene oxide copolymers; adjuvants; sugars, including sucrose, trehalose, and mannitol; synthetic sweeteners; menthol; and camphor.

Preferred devices are in the form of inhalers for pulmonary delivery of therapeutic compounds. However, the devices and methods of the present invention may be used in other applications where EHD aerosolization may be desired, including the spraying of insecticides, biocides, paint, cosmetics, etc. Depending on the voltage applied and the flow rate of the liquid supplied to the nozzle, the interaction between the cloud of charged ions and the charged droplets of liquid from the nozzle may lead to either partial or complete neutralization of any charge on the aerosol droplets. For pulmonary delivery (i.e., to the bronchioles and alveoli), it is preferred that the aerosol be completely neutralized. An aerosol that remains electrostatically charged may be preferred for other uses, such as applying insecticides, cosmetics and paint. A small amount of residual charge may also be preferred for delivery of therapeutics to the upper portions of the respiratory tract.

In devices in the form of inhalers, the flow of gas over the discharge electrode is typically provided by air traveling through a flow pathway that comprises an intake and an aerosol egress. The device may be fitted with a breath-activated switch, so that as the user inhales through the device, a voltage is simultaneously applied to the discharge electrode. Thus, the act of inhalation through the device provides for a flow of air that becomes electrostatically charged as it passes over the discharge electrode. Alternatively, another gas, from an alternative gas source, may be utilized, so long as the gas is one that is able to pick up sufficient charge to generate the necessary electric field in front of the nozzle. Alternative switching means, readily known to those of ordinary skill in the art, may be utilized instead of breath-activation to trigger activation of the device.

In embodiments where the device is an inhaler, the device is designed to produce aerosolized particles of respirable size. Preferably, the droplets have a diameter of less than or equal to about 6 microns, and more preferably, in the range of about 1-5 microns, for deep lung administration. Because many formulations are intended for deep-lung deposition, at least about 80% of the particles preferably have a diameter of less than or equal to about 5 microns for effective deep lung administration of the therapeutic agent. The aerosolized droplets are substantially the same size and have near zero velocity as they exit the apparatus.

Suitable characteristics of compositions for aerosolization and delivery by inhalation are described in Thurston et al., U.S. Pat. No. 6,503,481. Without limiting the scope of the invention, liquids having the following electrical and physical characteristics permit optimum performance by the device and method to generate a clinically relevant dose of respirable particles within a few seconds. The surface tension of the liquid typically is in the range of about 15-50 dynes/cm, preferably about 20-35 dynes/cm, and more preferably about 22-33 dynes/cm. Liquid resistivity typically is greater than about 200 ohm-meters, preferably greater than about 250 ohm-meters, and more preferably greater than about 400 ohm-meters (e.g., 1200 ohm-meters). The relative electrical permittivity typically is less than about 65, preferably less than about 45. Liquid viscosity typically is less than about 100 centipoise, preferably less than about 50 centipoise (e.g., 1 centipoise). Although the above combination of characteristics allows optimum performance, it may be possible to effectively spray liquids with one or more characteristics outside these typical values using the device and method of the invention. For example, certain nozzle configurations may allow effective spraying of less resistive (more conductive) liquids.

The range of volumes to be delivered by an inhaler is dependent on the specific drug formulation. Typical doses of pulmonary therapeutic agents are in the range of 0.1-100 µL. Ideally, the dose should be delivered to the patient during a single inspiration, although delivery during two or more inspirations may be acceptable under particular conditions. To achieve this, the device generally must be capable of aerosolizing about 0.1-50 µL, and particularly about 10-50 µL, of liquid in about 1.5-2.0 seconds. Delivery efficiency is also a major consideration for the pulmonary delivery device so liquid deposition on the surfaces of the device itself should be minimal. Optimally, 70% or more of the aerosolized volume should be available to the user.

As described in co-owned U.S. Pat. No. 6,503,481, referenced previously, and incorporated herein by reference in its entirety, the liquid composition to be sprayed by inhalers typically includes an active ingredient (also referred to herein as a "therapeutic agent"), and a liquid carrier for the active ingredient. The liquid compositions may also include an aerosol properties adjusting material, and/or an additional excipient. The combination of these components provides a therapeutic composition having enhanced properties for delivery to a user in an inhalable aerosol.

The number and types of therapeutic agents suitable for delivery to a patient by means of an inhaled aerosol varies widely and includes numerous options, including any of the following: chemo-therapeutic or chemopreventive agents; vaccines; nucleic acids, including DNA and RNA vectors and vaccines; aptamers; proteins; gene therapy agents for treating diseases such as cystic fibrosis; enzymes; hormones; antibodies; vitamins; peptides and polypeptides; oligonucleotides; cells; antigens; allergens; pulmonary surfactant and other surfactants (including synthetic surfactants); anti-infectious agents including antimicrobials, antibiotics, antifungals and antivirals; and pain management drugs. Preferred therapeutic agents include: corticosteroids, such as fluticasone; beta agonists, such as salmeterol; opiate analgesics, such as fentanyl; anticholinergics, such as scopolamine and nicotine; 5-HT3 serotonin antagonists, such as granisetron and ondansetron; selective serotonin (5-HT) receptor agonists, such as zolmitriptan; PDE-5 inhibitors, such as sildenafil and tadalafil; anti-fungals, such as voriconazole or amphotericin B; cannabinoid receptor antagonists, such as rimonabant and varenicline; immunosuppressants, such as tacrolimus and rapamycin; sodium channel blockers, such as lidocaine; and peptide hormones, such as insulin. Combinations of therapeutics may also be used, such as a combination of fluticasone and salmeterol, for the treatment of asthma or chronic obstructive pulmonary disease. Depending upon the particular therapeutic agent chosen, a pharmaceutically acceptable salt form of the agent, as are known to those of ordinary skill in the art may be preferred.

The composition to be aerosolized also includes a carrier in which the therapeutic agent may be dissolved, suspended or emulsified. A variety of solvents or emulsifying agents are suitable for this purpose. In a typical embodiment of the present invention, either water or ethanol (depending on the solubility characteristics of the active ingredient) is used as the solvent in which the therapeutic agent may be dissolved or suspended. In a preferred embodiment, the carrier (solvent) fraction of the composition may represent 5 to 95% of the total volume of the composition. In other embodiments, the fraction of the composition represented by the carrier varies depending on the solubility or insolubility of the active ingredient. For example, if an active ingredient is highly soluble in the carrier (e.g. water), then the carrier fraction of the total composition may be as low as about 5% to 10%. If an active ingredient is only moderately soluble in water, a larger fraction of water may be required to completely dissolve or sufficiently suspend the active ingredient.

The pH of desired solvent, as well as the pH of the entire composition, may impact the solubility and stability of the therapeutic agent. Although pH requirements are likely to differ among specific compositions depending on the active ingredient being used, pH ranges useful in the present invention for the liquid carrier may be in the range of pH about 2 to 9. Preferably, a pH range of about 3 to 8 is used, and most preferably a pH range of about 5 to 8 is used.

Preferably, the solvents selected as carriers are chosen for use as carriers based both on compatibility with the active ingredient and on their suitability for EHD aerosolization. Typically, the solvents include water or ethanol, or mixtures thereof. Therapeutic agents dissolved in ethanol, or mixtures of ethanol and water may be particularly good candidates for electrohydrodynamic spraying because the ethanol base has a low surface tension and is nonconductive. Ethanol also is an antimicrobial agent, which reduces the growth of microbes within the drug formulation and on the housing surfaces. Thus, carriers containing from about 50% ethanol by weight, from about 60% ethanol by weight, from about 70% ethanol by weight, from about 80% ethanol by weight, from about 90% ethanol by weight, from about 95% ethanol by weight or about 100% ethanol by weight may be used in various embodiments. Particularly useful carriers comprise solvent mixtures comprising greater than about 90% by weight ethanol and less than about 10% by weight water, or more specifically solvent mixtures comprising about 95% by weight ethanol and about 5% by weight water.

In an alternative embodiment, phospholipids or pulmonary surfactant may be used as a carrier. In still another embodiment, other alcohols such as isopropanol are employed as carriers. In other embodiments of the present invention, perfluoronated compounds such as perfluorooctanol and perfluorodecalin are substituted for some or all of the water or ethanol as the carrier material. Such perfluoronated compounds are useful as alternative carriers for drugs soluble in perfluoronated carriers, micro-suspended medicaments or emulsified mixtures of such pharmaceutical products in water.

The co-owned US 2004/0195403 A1, referenced previously, in one embodiment describes a pulmonary aerosol delivery device that utilizes a disassociated, upstream discharge electrode. Since the discharge electrode is upstream of the nozzle, and shielded from the nozzle by the presence of a nonconductive discharge shroud, wetting of the electrode from the spray nozzle is reduced, as compared with prior art devices. The instant device improves on that design by providing a conductive electric field shield between the nozzle and the discharge electrode. The conductive electric field shield may be prepared from a conductive metal, such as copper or steel, or from a suitable conductive polymer, such as a conductive grade of polycarbonate. An insulator disposed between the electric field shield and the discharge electrode prevents current leakage between these two conductors.

Figure 3:
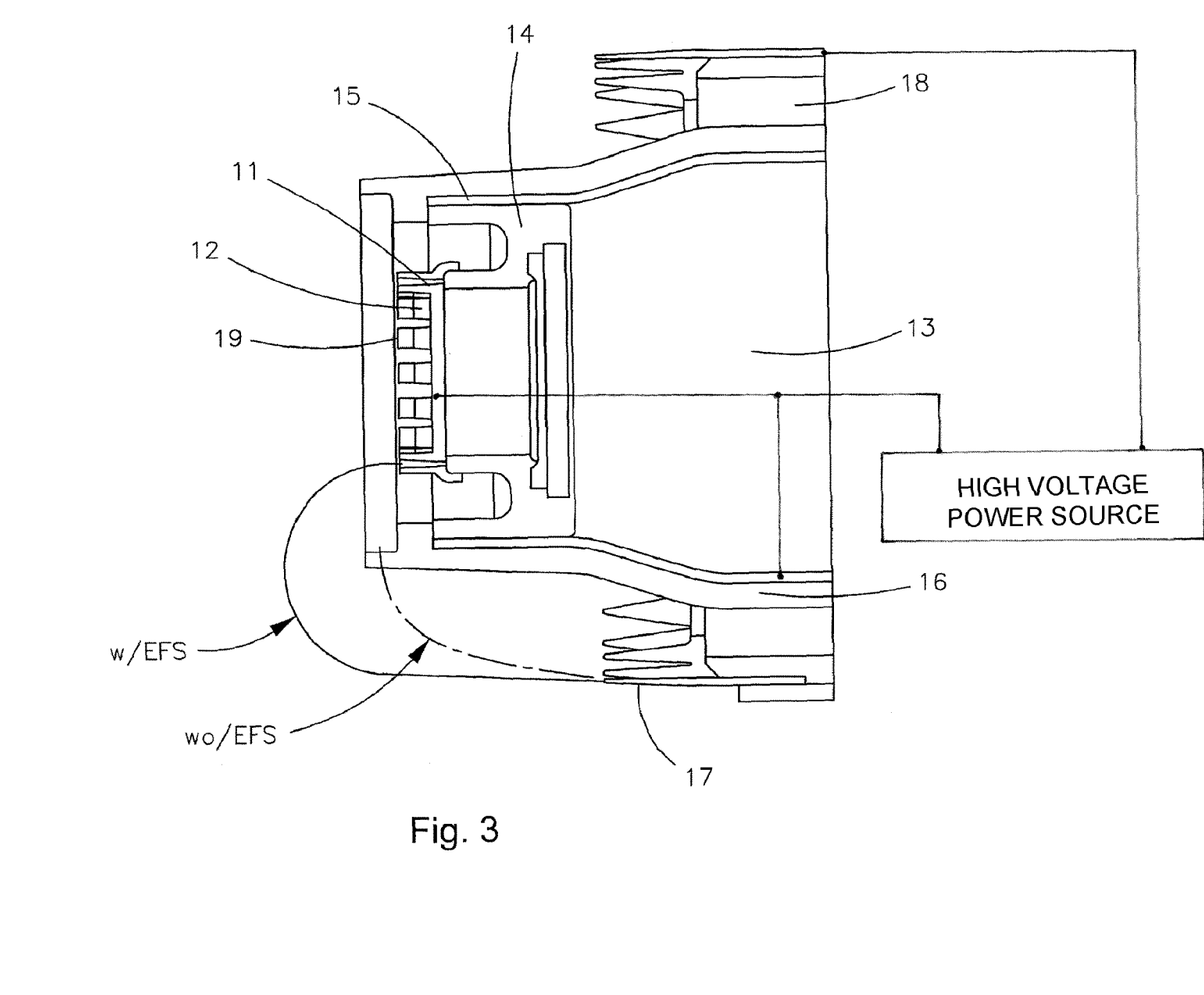
FIG. 3 depicts a longitudinal section of a device of the present invention, and highlights the improved electric field characteristics achieved therefrom.

One suitable configuration of these elements is shown in FIG. 3. This longitudinal section of the spray end of a typical device of the present invention comprises a nozzle (11) comprising a plurality of spray sites (12) arranged in an annular configuration. Liquid is supplied from the reservoir (13) through a supply tube (not shown) to the supply end of the nozzle. The nozzle is mounted on a conductive back (14) which is disposed within a conductive outer tube (15). Since both the conductive outer tube and the conductive back are electrically connected and at the same voltage potential, the two elements act in concert to serve as the electric field shield. In this embodiment, the conductive outer tube surrounds reservoir (13), and extends back into the device, where it makes electric contact with one side of a high voltage power supply. In an alternative embodiment, the conductive back may be connected to the power supply by a wire. In either embodiment, fluid from the supply tube contacts the conductive back at the perimeter of the nozzle. Thus, in these embodiments, fluid within the nozzle is electrically connected to the power supply, at the supply end of the nozzle.

The conductive outer tube is in turn disposed within an insulator (16), that serves to prevent leakage of current between discharge electrode (17) and conductive outer tube (15). In use, gas flows (from right to left in the figure) through a flow path (18) across the discharge electrode (17) towards an aerosol egress (not shown). In use, the application of electric charge provides a potential difference strong enough to cause Taylor cone formation in the liquid at the spray ends (19) of the nozzle spray sites (12).

Positioning an electric conductor having the same polarity as the liquid being sprayed adjacent to the nozzle alters the electric field created in the device, as also shown in FIG. 3. The dashed line represents the approximate electric field line as it would appear in the absence of the conductive shield, while the solid line represents the approximate electric field line in a device of the present invention. As the drawing shows, the conductive electric field shield helps redirect the electric field line so as not to "pull" the Taylor cones back towards the discharge electrode. As shown in this figure, the instant invention provides a more focused delivery of aerosol to be entrained into the flow of gas through the device, thereby producing less wetting of the discharge shroud and a more efficient and consistent delivery of greater doses of aerosolized liquid to the egress.

Figure 4:
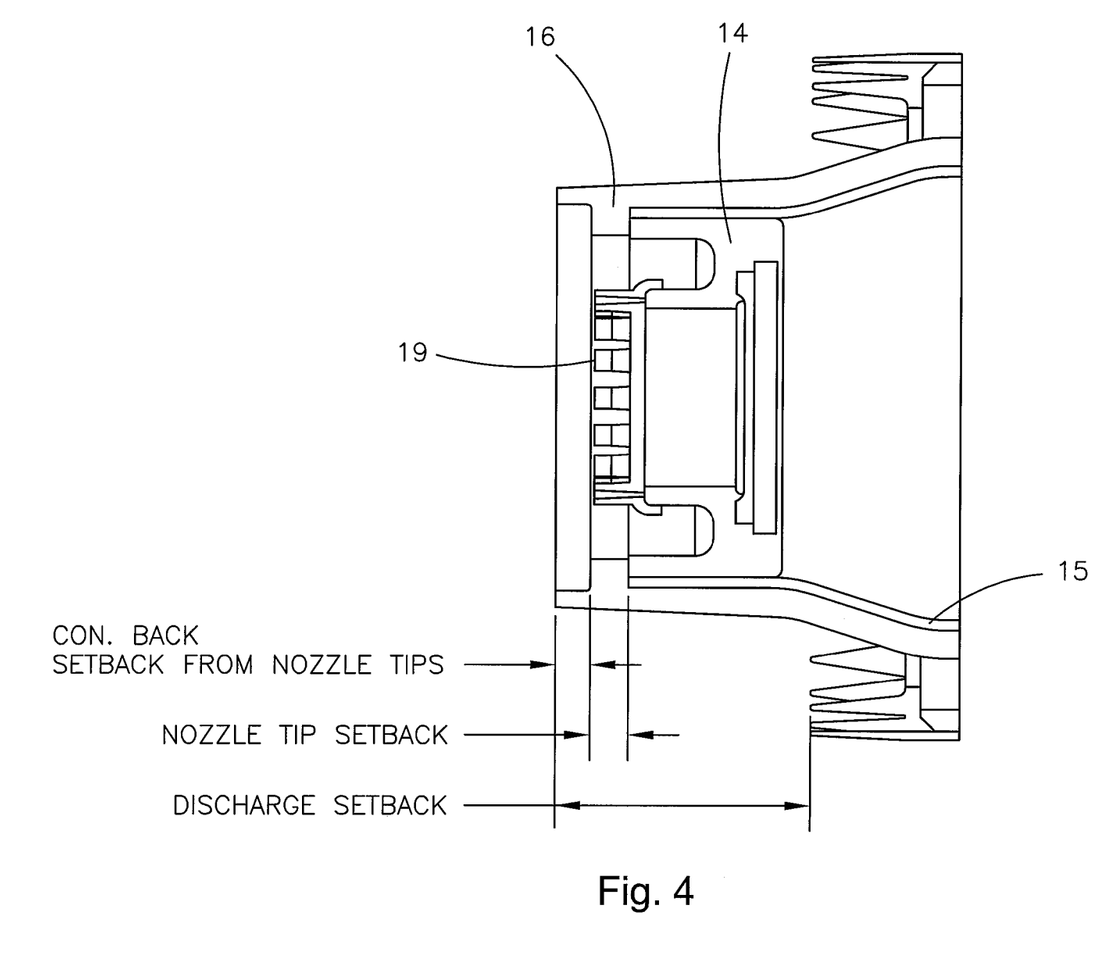
FIG. 4 depicts a longitudinal section of this same device, and highlights the relative location of elements of a particularly preferred embodiment of the device.

As shown in FIG. 4, in this preferred embodiment, the nozzle spray ends (19) are set back from the forward opening of the insulator by about 1 mm, and the conductive back (14) and conductive tube (15) are in turn set back from the spray ends (19) of the nozzle by 1 mm to 1.5 mm. The forward points of the discharge electrode are also set back from the forward opening of the insulator by about 7 mm to 9 mm. The distances of these set backs are appropriate for the radial dimensions of this particular device, in which the outside diameter of the nozzle is about 0.25 inches, the outside diameter of the forward opening of the insulator is about 0.48 inches, and the diameter of the discharge electrode is about 0.8 inches. The optimal set back distances would be expected to vary proportionally with changes in these diameters.

In an alternative embodiment, not shown, the nozzle may be mounted on a conductive back which is, itself, in electric connection with one pole of high voltage power supply. The back may be prepared from any suitable conductive material, including metal and conductive polymers, known to those of ordinary skill in the art.

In another alternative embodiment, the conductive back may be formed as shown in FIGS. 3 and 4, but the electric field shield, instead of being formed as a conductive outer tube, may be in the form of a cup having a base and a tubular side that terminates at a forward circular rim. Preferably, the cup is positioned such that the base is situated behind the conductive back, the tubular side surrounds the nozzle and conductive back, with the circular forward rim set back from the nozzle spray ends, and from the forward opening in the insulator, as described previously. The cup may then be electrically connected to the high voltage power supply, for example, by a wire.

FIGS. 3 and 4 also illustrate another feature of certain preferred embodiments of the present invention. As shown in these figures, insulator (16) and grounded conductive outer tube (15), though generally tubular in configuration, narrow or (neck) to a smaller diameter near their forward openings. Narrowing the diameter of the insulator and electric field shield in the proximity of the nozzle provides for improved flow of the gas that will entrain the aerosolized liquid. This improvement leads to less wetting of the insulator and a greater efficiency in delivery of aerosolized droplets to the aerosol egress. It will be appreciated that the terms "tube" and "tubular" are intended to cover this preferred embodiment. Accordingly, as used herein, these terms should be understood to refer to structures having a generally tubular shape, and include tubes of varying diameters, as shown in these figures.

The entire disclosure of each patent, patent application, and publication cited or described in this document is incorporated herein by reference, for all purposes.

When concentrations, amounts, percentages, and other numerical data are expressed or presented herein in a range format, it is to be understood that such a range format is used merely for convenience and brevity and thus should be interpreted flexibly to include not only the numerical values explicitly recited as the limits of the range, but also to include each of the individual numerical values or sub-ranges encompassed within that range as if each numerical value and sub-range is explicitly recited. As an illustration, a concentration range of "about 1 weight % to about 10 weight %" should be interpreted to include not only the explicitly recited concentration of about 1 weight % to about 10 weight %, but also individual concentrations and the sub-ranges within the indicated range. Thus, included in this numerical range are individual concentrations such as 2 weight %, 5 weight %, and 8 weight %, and sub-ranges such as from 1 weight % to 3 weight %, from 5 weight % to 9 weight %, etc. As used herein, the term "about" means plus or minus approximately ten percent of the indicated value, such that "about 50% by weight" indicates approximately 45% to 55% by weight.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A device for dispensing an aerosolized liquid comprising:
   a flow pathway extending between an upstream gas intake and a downstream aerosol egress;
   at least one nozzle having a supply end and a forward spray end, said at least one nozzle disposed within said flow pathway and adapted to spray an aerosolized liquid toward said downstream aerosol egress;
   a voltage power source having a first pole and a second pole;
   at least one discharge electrode operatively connected to the first pole of said voltage power source, said at least one discharge electrode disposed within said flow pathway upstream of said at least one nozzle;
   a conductive electric field shield disposed between said spray end of said at least one nozzle and said at least one discharge electrode, said shield operatively connected to ground or to the second pole of said power source;
   an insulator disposed between said at least one discharge electrode and said conductive electric field shield;
   a liquid supplier operatively connected to the supply end of said at least one nozzle; and
   a liquid to be aerosolized, said liquid electrically connected to ground or to the second pole of said power source.

2. The dispensing device of claim 1, wherein said at least one nozzle comprises a plurality of spray sites.

3. The dispensing device of claim 2, wherein said plurality of spray sites are annularly arranged.

4. The dispensing device of claim 1, wherein said at least one nozzle is electrically non-conductive.

5. The dispensing device of claim 1, wherein said at least one discharge electrode carries a positive electric charge and said electric field shield carries a negative electric charge.

6. The dispensing device of claim 1, wherein said at least one discharge electrode carries a positive electric charge and said electric field shield is operatively connected to ground.

7. The dispensing device of claim 1, wherein an electric potential between said at least one discharge electrode and said electric field shield is from about 5 kV to about 15 kV.

8. The dispensing device of claim 1, further comprising a liquid within said at least one nozzle.

9. The dispensing device of claim 8, wherein said liquid within said at least one nozzle is electrically connected to said electric field shield.

10. The dispensing device of claim 9, further comprising an electrically conductive back electrically connected to said electric field shield, wherein said at least one nozzle is mounted on said back in a manner that liquid supplied to said nozzle is in electric contact with said back.

11. The dispensing device of claim 8, wherein said liquid is in the form of a solution, a suspension, or an emulsion.

12. The dispensing device of claim 11, wherein said liquid is an insecticide or a biocide.

13. The dispensing device of claim 11, wherein said liquid is a nutrient.

14. The dispensing device of claim 11, wherein said liquid is paint.

15. The dispensing device of claim 8, wherein said liquid is a medicament.

16. The dispensing device of claim 15, wherein said medicament comprises an active ingredient selected from the group consisting of fluticasone, salmeterol, fentanyl, scopolamine, nicotine, granisetron, ondansetron, zolmitriptan, sildenafil, tadalafil, voriconazole, amphotericin B, rimonabant, varenicline, tacrolimus, rapamycin, lidocaine, insulin, and pharmaceutically acceptable salts thereof.

17. The dispensing device of claim 1, wherein said flow pathway defines a longitudinal axis, and said at least one discharge electrode, said insulator, said electric field shield, and said at least one nozzle are positioned substantially coaxially within said flow pathway, about said longitudinal axis.

18. The dispensing device of claim 17, wherein said insulator further comprises a substantially tubular body having a circular forward opening at a forward end of the body.

19. The dispensing device of claim 18, wherein said at least one nozzle is positioned substantially concentrically within said insulator.

20. The dispensing device of claim 19, wherein said at least one nozzle comprises a plurality of annularly arranged spray sites each having a spray end, wherein said spray ends are set back from said forward opening of said insulator.

21. The dispensing device of claim 20, wherein said spray ends are set back from said forward opening of said insulator by a distance of about 0.5 mm to about 1.5 mm.

22. The dispensing device of claim 19, wherein said electric field shield comprises a substantially tubular body having a circular forward opening at a forward end of the body, and said electric field shield is positioned substantially concentrically between said insulator and said at least one nozzle.

23. The dispensing device of claim 22, wherein said forward opening of said electric field shield is set back from said forward opening of said insulator by a distance of from about 1.5 mm to about 3.0 mm.

24. The dispensing device of claim 22, wherein said at least one discharge electrode comprises an annular band having a plurality of sharply pointed projections extending forward along said longitudinal axis, and is disposed within said air flow pathway external of and coaxial to said insulator.

25. The dispensing device of claim 24, wherein a forward end of said sharply pointed projections are set back from said forward opening of said insulator by a distance of from about 6 mm to about 10 mm.

26. The dispensing device of claim 25, wherein said at least one nozzle spray end is set back from said forward opening of said insulator by a distance of about 0.5 mm to about 1.5 mm and said forward opening of said electric field shield is set back from said forward opening of said insulator by a distance of from about 1.5 mm to about 3.0 mm.

27. The dispensing device of claim 22, wherein a body portion of said insulator has a first insulator diameter and said circular forward opening has a second insulator diameter that is less than said first insulator diameter, and a body portion of said electric field shield has a first shield diameter and said circular forward opening of said electric field shield has a second shield diameter that is less than said first shield diameter.

28. The dispensing device of claim 27, wherein said second diameters are from about 50% to about 80% of said first diameters.

29. The dispensing device of claim 1, wherein said device is an inhaler.

30. A method of providing an aerosol, said method comprising:
(a) providing a device comprising:
a flow pathway extending between an upstream gas intake and a downstream aerosol egress;
at least one nozzle having a supply end and a forward spray end, said at least one nozzle disposed within said flow pathway;
a voltage power source having a first pole and a second pole;
at least one discharge electrode operatively connected to the first pole of said voltage power source, said at least one discharge electrode disposed within said flow pathway upstream of said at least one nozzle;
a liquid supplier operatively coupled to said at least one nozzle and supplying liquid to said at least one nozzle;
a conductive electric field shield disposed between said spray end of said at least one nozzle and said at least one discharge electrode, said shield operatively connected to ground or to the second pole of said voltage power source; and
an insulator disposed between said at least one discharge electrode and said conductive electric field shield;
wherein at least one of said nozzle and said liquid is electrically connected to said electric field shield;
(b) initiating flow of a gas through said flow pathway and supplying liquid to said at least one nozzle; and
(c) applying voltage to said at least one discharge electrode in an amount sufficient to ionize at least a portion of said gas, wherein an electric field created by a difference in electric potential between said at least one discharge electrode and said liquid is of sufficient intensity to aerosolize said liquid.

31. The method of claim 30, wherein said device is an inhaler, said gas is air, and said liquid is a medicament.

32. The method of claim 31, wherein said discharge electrode carries a positive electric charge of from about 5 kV to about 15 kV and said electric field shield is operatively connected to ground.

33. The method of claim 31, wherein said at least one discharge electrode carries a positive electric charge and said electric field shield carries a negative electric charge, and a potential difference between the positive and negative electric charges is from about 5 kV to about 15 kV.

34. The method of claim 31, wherein said at least one nozzle is electrically non-conductive, and said at least one nozzle is mounted on an electrically conductive back such that the liquid being supplied to said at least one nozzle comes into contact with said electrically conductive back, and said electrically conductive back is operatively connected to said electric field shield.

35. The method of claim 31, wherein said medicament comprises an active ingredient selected from the group consisting of fluticasone, salmeterol, fentanyl, scopolamine, nicotine, granisetron, ondansetron, zolmitriptan, sildenafil, tadalafil, voriconazole, amphotericin B, rimonabant, varenicline, tacrolimus, rapamycin, lidocaine, insulin, and pharmaceutically acceptable salts thereof.

36. The method of claim 30, wherein substantially all of the aerosol delivered to the aerosol egress is electrically neutral.

37. The method of claim 30, wherein a portion of the aerosol delivered to the aerosol egress is electrically charged.

38. An electrohydrodynamic spraying method comprising:
a. supplying a liquid to be sprayed as an aerosol to a nozzle having a supply end and a plurality of spray ends;
b. supplying a voltage power source having a first pole and a second pole;
c. applying a voltage from the first pole of said voltage power source to a discharge electrode positioned upstream of said nozzle;
d. transporting a gas across said discharge electrode to create a cloud of positively charged ions in the vicinity of said nozzle;
e. positioning a conductive electric field shield in electric communication with said liquid between at least one of said spray ends of said nozzle and said discharge electrode, wherein said electric field shield is at ground potential or supplied with a voltage from the second pole of said voltage power source.

39. The method of claim 38 further comprising forming said nozzle from an electrically nonconductive material.

40. The method of claim 39 further comprising providing an electrically conductive back, mounting said nozzle on said back, and electrically coupling said back to said electric field shield.

41. The method of claim 38 wherein said electric field shield is at ground potential and said voltage applied to said discharge electrode is a positive charge of from about 5 kV to about 15 kV.

42. The method of claim 38 wherein a positive electric charge is applied to said discharge electrode and a negative electric charge is applied to said electric field shield, wherein an electric potential between the positive and negative electric charges is from about 5 kV to about 15 kV.

43. The method of claim 38 wherein said step of transporting a gas is provided by inhaling air.

* * * * *